(12) United States Patent
Kang

(10) Patent No.: US 8,513,451 B2
(45) Date of Patent: Aug. 20, 2013

(54) FLUORESCENT PHOSPHOLIPASE $A_2$ INDICATORS

(76) Inventor: Hee Chol Kang, Eugene, OR (US)

( * ) Notice: Subject to any disclaimer, the term of this patent is extended or adjusted under 35 U.S.C. 154(b) by 468 days.

(21) Appl. No.: 12/602,388

(22) PCT Filed: May 30, 2008

(86) PCT No.: PCT/US2008/065432
§ 371 (c)(1),
(2), (4) Date: Apr. 9, 2010

(87) PCT Pub. No.: WO2008/151089
PCT Pub. Date: Dec. 11, 2008

(65) Prior Publication Data
US 2010/0203564 A1 Aug. 12, 2010

Related U.S. Application Data

(60) Provisional application No. 60/940,799, filed on May 30, 2007.

(51) Int. Cl.
*C07F 9/02* (2006.01)
*C07D 207/00* (2006.01)
*C12Q 1/34* (2006.01)

(52) U.S. Cl.
USPC .............................. 558/72; 548/405; 435/18

(58) Field of Classification Search
None
See application file for complete search history.

(56) References Cited

U.S. PATENT DOCUMENTS

| | | |
|---|---|---|
| 4,603,209 A | 7/1986 | Tsien et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,945,171 A | 7/1990 | Haugland et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,433,896 A | 7/1995 | Kang et al. |
| 5,442,045 A | 8/1995 | Haugland et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |

(Continued)

FOREIGN PATENT DOCUMENTS

WO  WO-2008/151089  12/2008

OTHER PUBLICATIONS

U.S. Appl. No. 09/969,583, filed Oct. 4, 2001, Myers, Kenneth J.

(Continued)

*Primary Examiner* — Karl J Puttlitz
(74) *Attorney, Agent, or Firm* — Life Technologies Corporation

(57) ABSTRACT

Compositions, methods of synthesis and applications of phospholipase $A_2$ (PLA$_2$) specific enzyme substrates which exhibit fluorescence resonance energy transfer (FRET) are described. The compounds generally have the structure: (I) wherein, the variables are described throughout the application. These novel compounds provide a sensitive method to monitor real time PLA$_2$ specific enzyme activities in various cells, tissues and small organisms with fluorescence-ratiometric analysis.

32 Claims, 5 Drawing Sheets

(56) References Cited

U.S. PATENT DOCUMENTS

| | | |
|---|---|---|
| 5,569,766 A | 10/1996 | Waggoner et al. |
| 5,627,027 A | 5/1997 | Waggoner |
| 5,656,554 A | 8/1997 | Desai et al. |
| 5,696,157 A | 12/1997 | Wang et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,863,727 A | 1/1999 | Lee et al. |
| 5,945,526 A | 8/1999 | Lee et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,048,982 A | 4/2000 | Waggoner et al. |
| 6,080,852 A | 6/2000 | Lee et al. |
| 6,130,101 A | 10/2000 | Mao et al. |
| 6,140,494 A | 10/2000 | Hamilton et al. |
| 6,162,931 A | 12/2000 | Gee et al. |
| 6,184,379 B1 | 2/2001 | Josel et al. |
| 6,221,606 B1 | 4/2001 | Benson et al. |
| 6,229,055 B1 | 5/2001 | Klaubert et al. |
| 6,335,440 B1 | 1/2002 | Lee et al. |
| 6,339,392 B1 | 1/2002 | Ashihara et al. |
| 6,348,599 B1 | 2/2002 | Cummins et al. |
| 6,358,684 B1 | 3/2002 | Lee |
| 6,372,445 B1 | 4/2002 | Davis et al. |
| 6,403,807 B1 | 6/2002 | Singh et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,977,305 B2 | 12/2005 | Leung et al. |
| 2003/0135869 A1* | 7/2003 | Farber et al. ............ 800/3 |
| 2004/0171096 A1 | 9/2004 | Ferguson |

OTHER PUBLICATIONS

Farber, S. A. et al., "Genetic Analysis of Digestive Physiology Using Fluorescent Phospholipid Reporters", *Science*, vol. 292, pp. 1385-1388 (2001).

Hendrickson, H. S. et al., "Intramolecularly Quenched BODIPY-Labeled Phospholipid Analogs in Phospholiphase A2 and Platelet-Activating factor Acetylhydrlase Assays and in Vivo Flouroscence Imaging", *Analytical Biochemistry* vol. 276, pp. 27-35 (1999).

Monti, J. A. et al., "Synthesis and properties of a highly flourescent derivative of phosphatidylethanomine", *J. of Lipid Research*, vol. 19, pp. 222-228 (1978).

PCT/US08/065432 ISR, mailed Dec. 4, 2008.

PCT/US08/065432 PCT Written Opinion mailed Dec. 4, 2008.

Feng, Manabe, Shope, Widmer, Dewald, Prestwich, "A Real-Time Fluorogenic Phospholipase A2 Assay for Biochemical and Cellular Activity Measurements", *Chemistry & Biology*, vol. 9, pp. 795-803 (2002).

Rose and Prestwich, "Fluorogenic Phospholipids as Head Group-Selective Reporters of Phospholipase A Activity", *ACS Chemical Biology*, vol. 1, pp. 83-92 (2006).

Wichmann, Wittbradt and Schultz, "A Small-Molecule FRET Probe to Monitor Phospholipase A2 Activity in Cells and Organisms", *Angewandte Chemie International Edition in English*, vol. 45, pp. 508-512 (2006).

Wichmann, O., "FRET Probes to monitor Phospholiphase A2 Activity", *Chem. Commun*, pp. 2500-2501 (2001).

\* cited by examiner

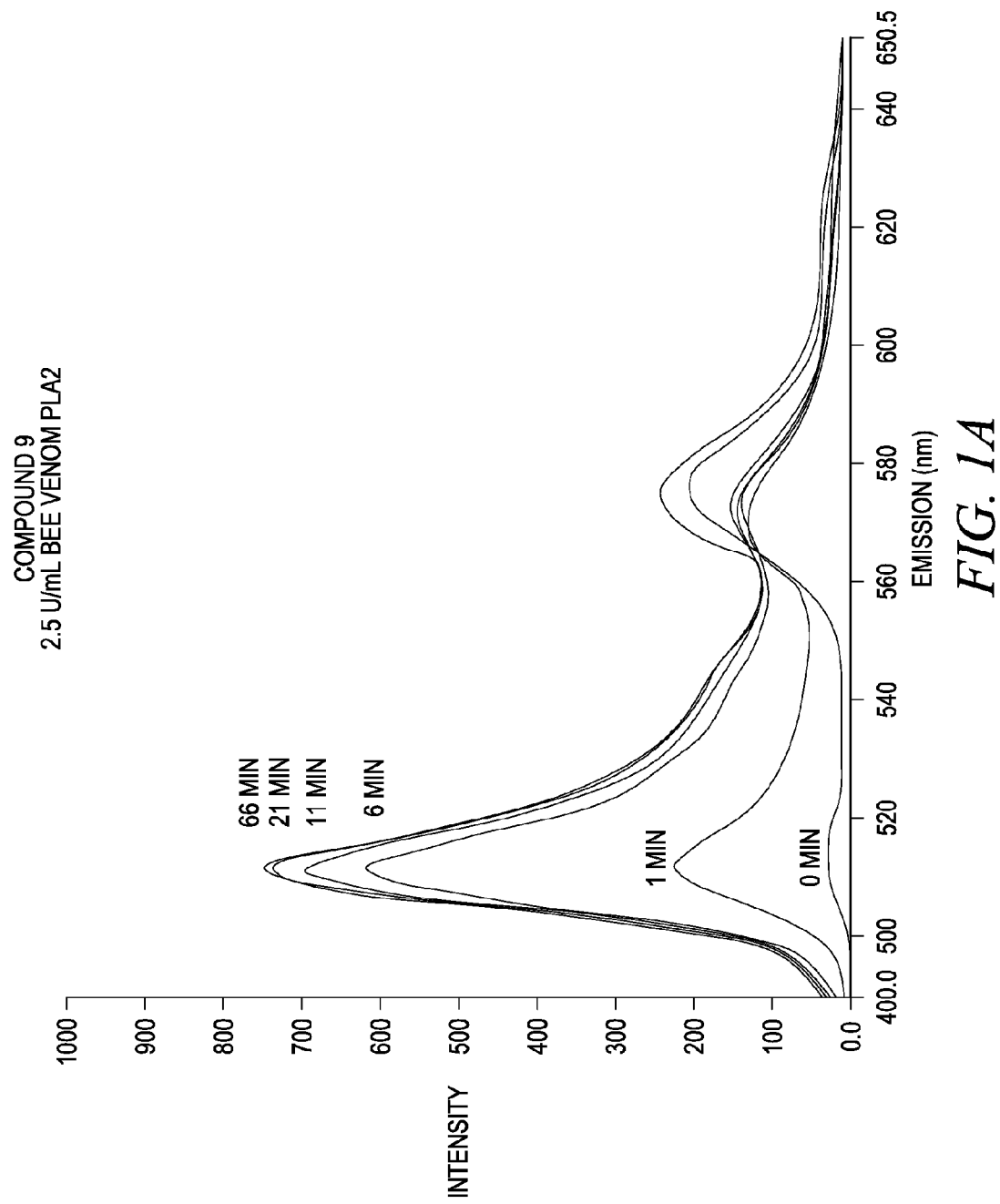

FLUORESCENT PHOSPHOLIPASE A$_2$ INDICATORS

FIELD OF THE INVENTION

The present invention relates generally to compositions comprising a substrate for phospholipase A$_2$ (PLA$_2$) operably connected to a FRET pair comprising a donor and acceptor molecule, at least one of which is amenable to cleavage by PLA$_2$ thereby resulting in a fluorescent response.

BACKGROUND OF THE INVENTION

Phospholipase A$_2$ (PLA$_2$) represents a superfamily of intracellular and secreted enzymes that hydrolyze the sn-2 ester linkage of phospholipids. It has been well known that PLA$_2$ plays important roles in many human diseases, including cardiovascular diseases, neurological disorders and cancer. Even though many methods (e.g. colorimetric, radioactive, fluorogenic) have been developed to monitor the activity of PLA$_2$ there are many limitations for their uses, in particular, real-time continuous monitoring in living cells.

Recently Schultz and his coworkers described the PLA$_2$ substrate based on fluorescence resonance energy transfer which appears to be a versatile quantitative real-time assay for PLA$_2$ with fluorescence ratiometric analysis and selectivity for specific PLA$_2$ in living cells. *Agnew. Chem. Int. Ed.*, 2006, v. 45, pgs. 508-512. Schultz covalently attached NBD fluorophore as a donor at sn-1 position with nonhydrolyzable ether linkage and Nile Red at sn-2 position as an acceptor with ester bond (A).

While this substrate is reported to be useful for monitoring real-time activity of PLA$_2$ in living cells, it has significant limitations due to the low photostability and low fluorescence quantum yield (QY) of the fluorophores (NBD and Nile Red) in particular for fluorescence imaging applications. In addition NBD and Nile Red are both enviroment-sensitive dyes, so the signal intensity and wavelength are biased by environmental factors.

Accordingly an objective of the present invention is to provide an improved PLA$_2$ selective enzyme substrate with high fluorescence QY and greater photostability.

SUMMARY OF THE INVENTION

Polyazaindacene fluorophores, such as 4,4-difluoro-4-bora-3a,4a-diaza-s-indacene (BODIPY), are highly fluorescent with high extinction coefficient, narrow emission, neutral and insensitive to environment and with high photostability. In a preferred embodiment of the invention, a polyazaindacene, such as BODIPY is covalently attached at sn-1 position with nonhydrolyzable ether linkage as an acceptor, which excludes the substrate property for PLA$_1$ and other unspecific lipases. A second polyazaindacene, such as BODIPY, which is a donor is appended with an ester linkage at the sn-2 position which makes it labile and specific for PLA$_2$.

By constructing the molecule this way, fluorescence resonance energy transfer (FRET) occurs which emits distinct fluorescent profile before and after cleavage by PLA$_2$. PLA$_2$ cleavage results in immediate increase of donor fluorescence and decrease the acceptor fluorescence, which can be utilized monitoring the degree of PLA$_2$ activity by a fluorescence ratiometric analysis. The fluorescence wavelengths can be tunable with wide ranges which cover visible to near IR regions by properly choosing a donor and acceptor pair.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

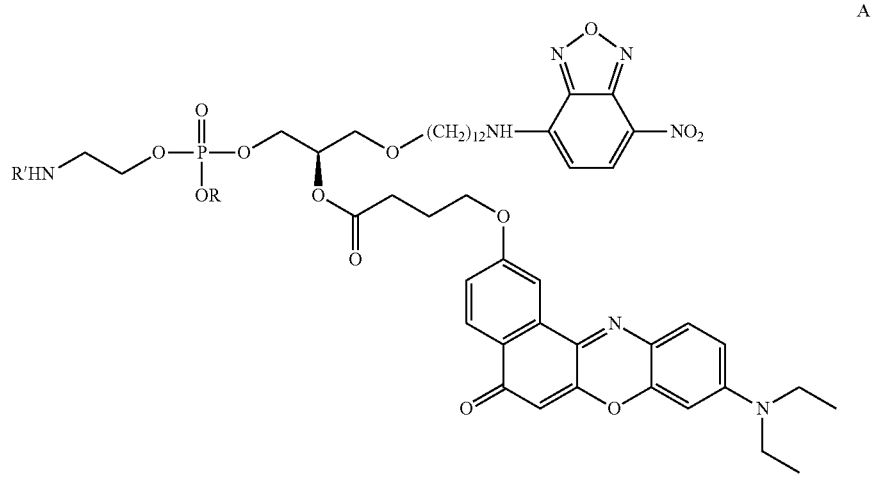

A

BRIEF DESCRIPTION OF THE DRAWINGS

FIGS. 1A and 1B depicts fluorescence intensity ratio change, 512/574 nm, plotted over time.

DETAILED DESCRIPTION OF THE INVENTION

Introduction

Figure 1B:
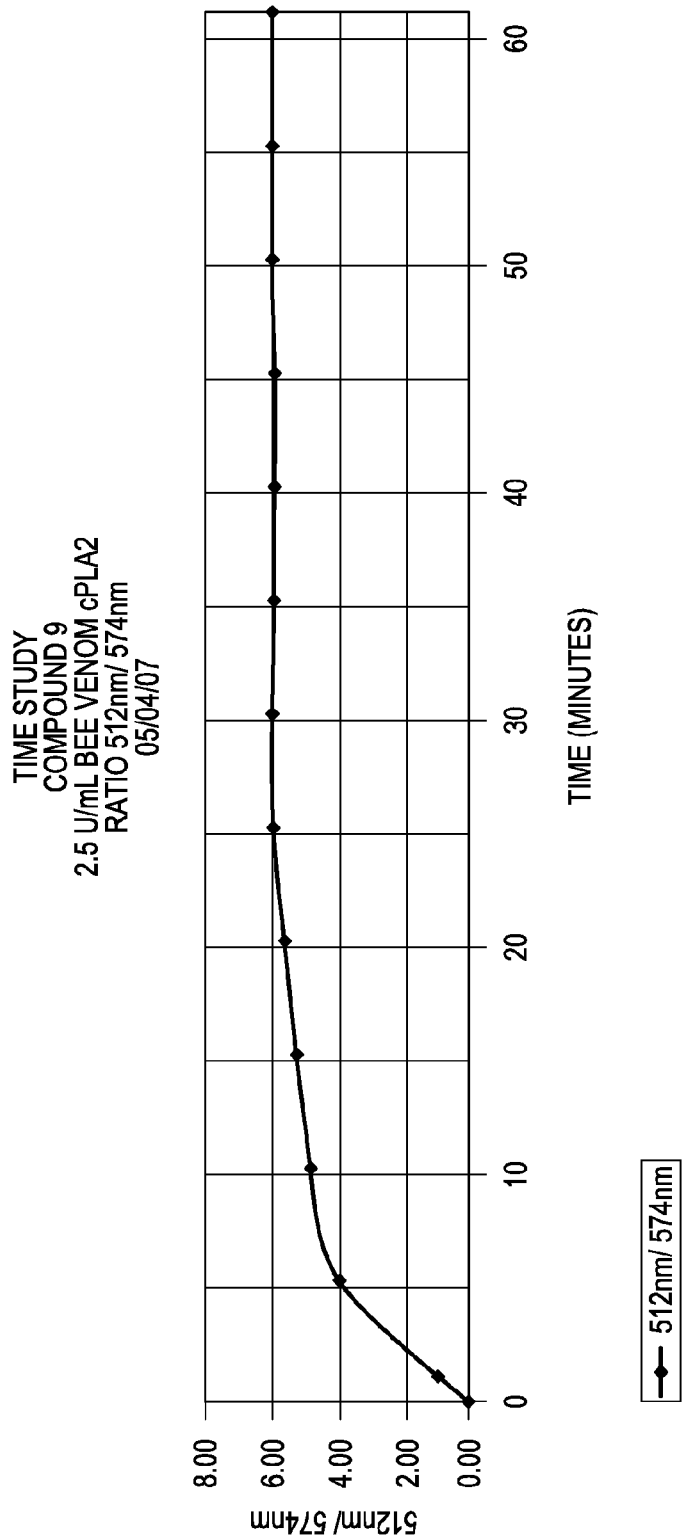

The instant invention provides compounds, methods of synthesis and applications for phospholipase $A_2$ ($PLA_2$) specific enzyme substrates which exhibit fluorescence resonance energy transfer (FRET). In particular, these compounds provide a sensitive method to monitor real time $PLA_2$ specific enzyme activities in various cells, tissues and small organisms with fluorescence-ratiometric analysis.

Specific advantages of the compounds described herein include: selectivity for $PLA_2$ enzymes (not for $PLA_1$), ratiometric real time in-situ measurement of $PLA_2$ enzyme activity, greater photostability especially for fluorescence microscopy applications, greater spectral match of the donor and acceptor pair with higher fluorescence quantum yield and narrower emission, and differentiated fluorescence signatures of cleavage products for imaging applications with tunable wavelengths from visible to near IR regions.

Scheme 1 illustrates cleavage of a BODIPY dye in a FRET pair as a result of $PLA_2$ enzymatic activity:

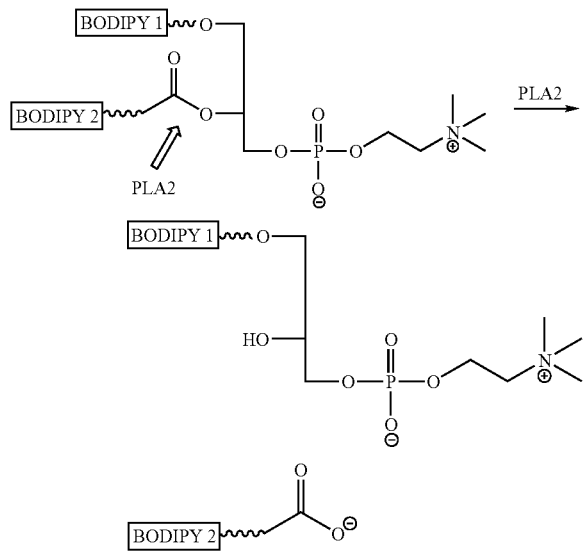

Scheme 1

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a compound" includes a plurality of compounds and reference to "a cell" includes a plurality of cells and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.) VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups NRC(O)alkyl, —NRC(O) substituted alkyl, —NRC(O)cycloalkyl, —NRC(O) substituted cycloalkyl, —NRC(O)cycloalkenyl, —NRC(O) substituted cycloalkenyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O) substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O) which is equivalent to —C(=O).

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazole, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

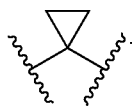 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

A dashed line projecting from a substituent, such as:

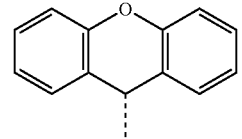

indicates the point of attachment to the base molecule. For a fused ring, dashed lines indicate portions of the base molecule where the fused ring is attached, such as:

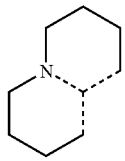

wherein the full molecule could have the structure:

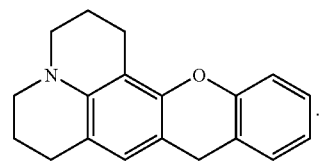 [SMILES: c1ccc2c(c1)Cc1cc3c4c(c1O2)CCCN4CCC3]

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

"Patient," "subject" or "individual" refers to mammals and includes humans and non-human mammals, such as monkeys, dogs, cats, horses, cows, pigs or rats.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "fluorophore" as used herein refers to a composition that is inherently fluorescent. Preferred fluorophores of the present invention include fluorescent dyes having a high quantum yield in aqueous media. Exemplary fluorophores include xanthene, indole, borapolyazaindacene, furan, and benzofuran, among others. The fluorophores of the present invention may be substituted to alter the solubility, spectral properties or physical properties of the fluorophore.

As used herein, "NBD" refers to 7-nitrobenzo-2-oxa-1,3-diazole amine and "Nile Red" refers to 9-diethylamino-5H-benzo[a]phenoxazin-5-one or it's 2-hydroxy derivative.

As used herein, "operably connected" refers to a $PLA_2$-cleavable covalent attachment. The attachment binds a $PLA_2$ substrate to a FRET pair comprising an acceptor and donor molecule, wherein $PLA_2$ cleaves one of the acceptor or donor molecule resulting in a shift in the emission spectra from red to green.

The term "Linker" or "L", as used herein, refers to a single covalent bond or a series of stable covalent bonds incorporating 1-20 nonhydrogen atoms selected from the group consisting of C, N, O, S and P that covalently attach the fluorophores to the PLA2 substrate. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a donor or acceptor of the present invention, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid. In the present invention the donor is cleaved from the acceptor by the phospholipase enzyme, which is selective for the $PLA_2$ substrate.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The Compounds

In general, for ease of understanding the present invention, the compounds and corresponding substituents will first be described in detail, followed by the many and varied methods in which the compounds find uses, which is followed by exemplified methods of use and synthesis of certain novel compounds that are particularly advantageous for use with the methods of the present invention.

One aspect of the present invention provides a compound comprising:
  a substrate for phospholipase $A_2$ ($PLA_2$) operably connected to a FRET pair comprising a donor and acceptor molecule having a first signal, wherein one of the donor or acceptor is cleaved by $PLA_2$ and not phospholipase $A_1$ ($PLA_1$), wherein cleavage by $PLA_2$ results in a second signal;
  with the proviso that the FRET pair does not comprise NBD or Nile Red.

This compound, when in contact with a $PLA_2$ enzyme cleaves the substrate, effectively separating the FRET pair, herein referred to as "de-FRETing", and shifting, or changing, the emitted wavelength. FRET occurs when a suitable fluorescent energy donor and an energy acceptor moiety are in close proximity to one another. The excitation energy absorbed by the donor is transferred to the acceptor which can then further dissipate this energy either by fluorescent emission if a fluorophore, or by non-fluorescent means if a quencher. A donor-acceptor pair comprises two fluorophores having overlapping spectra, where the donor emission overlaps the acceptor absorption, so that there is energy transfer from the excited fluorophore to the other member of the pair. For the purposes of this application, a FRET pair does not include a quencher such that when the substrate is intact there is no signal and a signal is generated when the substrate is cleaved because the quencher is separated from the fluorophore. In the present application the FRET pair has one signal when the substrate is intact and a second signal when the enzyme has cleaved the PLA$_2$ substrate.

The present compounds can function as a ratiometric PLA$_2$ substrate wherein the compounds emit at one wavelength in the absence of the enzyme and at another in the presence of the enzyme. This is particularly advantageous when detecting low concentrations of enzyme. Thus, any FRET pair wherein the energy is not quenched by the acceptor is part of the invention including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554, with the proviso that the dye pair is not NBD and Nile red.

Selected fluorophores, which can be paired with an appropriate fluorophore to form a FRET pair, include any chemical moiety that exhibits an absorption maximum beyond 280 nm. Dyes of the present invention include, without limitation; a pyrene, an anthracene, a naphthalene, an acridine, a stilbene, an indole or benzindole, an oxazole or benzoxazole, a thiazole or benzothiazole, a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, or sulfo. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, borapolyazaindacene, indole and derivatives thereof. The choice of the fluorophore attached to the PLA$_2$ substrate will determine the compound's absorption and fluorescence emission properties.

In one aspect the fluorophore contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art. In one aspect the fluorophore is a borapolyazaindacene that comprises one or more aryl or heteroaryl rings.

In another aspect of the invention, the compound has the formula:

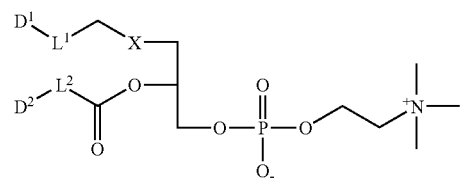

wherein,
D$^1$ is a borapolyazaindacene fluorophore;
D$^2$ is a borapolyazaindacene fluorophore;
L$^1$ is a linker;
L$^2$ is a linker; and
X is —O—, —S— or —NH—;
or a salt, stereoisomer, or tautomer thereof;
wherein D$^1$ and D$^2$ exhibit fluorescence resonance energy transfer (FRET) that is not quenched.

In another more particular embodiment thereof, D$^1$ is a donor and D$^2$ is an acceptor. In another embodiment, D$^1$ is a 4,4-difluoro-4-bora-3a,4a-diaza-s-indacene (BODIPY). More particularly, D$^2$ is a 4,4-difluoro-4-bora-3a,4a-diaza-s-indacene (BODIPY). In another embodiment, D$^2$ is substituted with an aryl or heteroaryl group.

In another embodiment D$^1$ is:

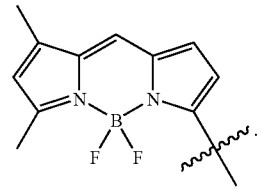

In another more particular embodiment, D$^2$ is:

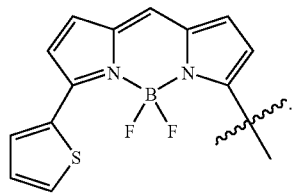

In another embodiment, X is —O—. In another embodiment, L$^1$ is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. More particularly, L$^1$ is -alkyl- or -substituted alkyl-. In another embodiment, L$^2$ is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. More particularly, $L^2$ is -alkyl- or -substituted alkyl-. More particular still, $L^1$ and $L^2$ are independently —$C_{3-8}$ alkyl-.

In another aspect of the invention, the compound has the formula:

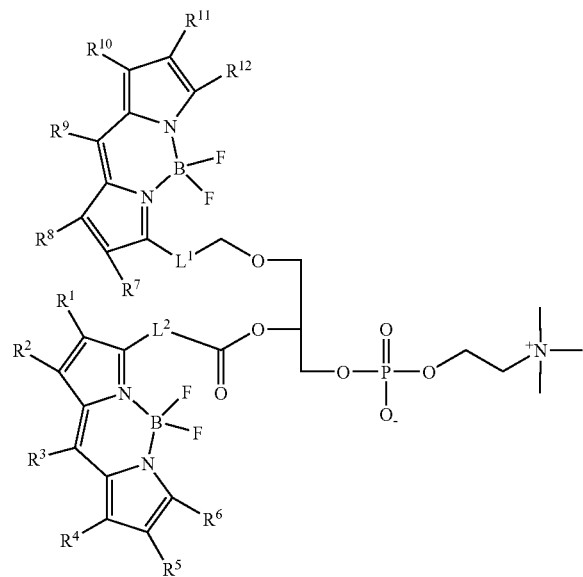

wherein,
$L^1$ is a linker;
$L^2$ is a linker;
$R^1$, $R^2$, $R^3$, $R^4$, $R^5$ and $R^6$ are each independently selected from the group consisting of H, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^7$, $R^8$, $R^9$, $R^{10}$, $R^{11}$ and $R^{12}$ are each independently selected from the group consisting of H, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another more particular embodiment thereof, $R^1$, $R^2$, $R^3$, $R^4$, $R^5$ and $R^6$ are each independently selected from the group consisting of H, halo, alkyl or substituted alkyl. In another embodiment, $R^7$, $R^8$, $R^9$, $R^{10}$, $R^{11}$ and $R^{12}$ are each independently selected from the group consisting of H, aryl, substituted aryl, heteroaryl, substituted heteroaryl. In another embodiment, at least one of $R^7$, $R^8$, $R^9$, $R^{10}$, $R^{11}$ and $R^{12}$ is aryl, substituted aryl, heteroaryl, substituted heteroaryl. In another embodiment, $R^6$ is heteroaryl. More particularly, $R^6$ is thiophenyl. In another embodiment, $R^1$, $R^2$, $R^3$, $R^4$ and $R^5$ are H. In another embodiment, $R^{10}$ and $R^{12}$ are methyl. In another embodiment, $R^7$, $R^8$, $R^9$, and $R^{11}$ are H.

In another embodiment, $L^1$ and $L^2$ are each independently a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. More particularly, $L^1$ and $L^2$ are each independently -alkyl- or -substituted alkyl-. More particular still, $L^1$ and $L^2$ are independently —$C_{3-8}$ alkyl-.

In another aspect of the invention, the compound has the formula:

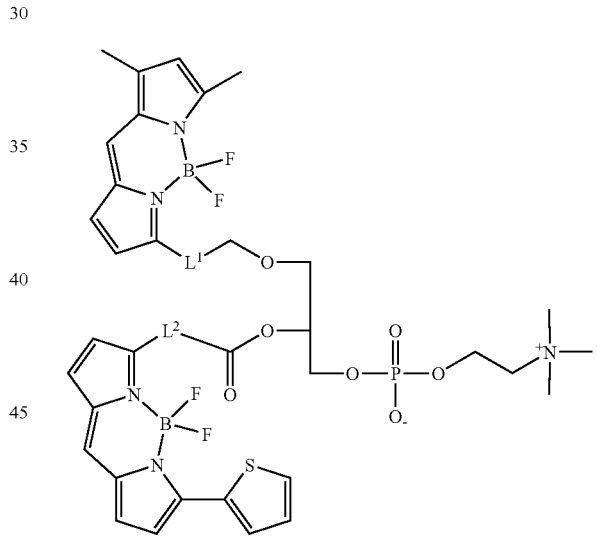

wherein,
$L^1$ is a linker; and
$L^2$ is a linker.

More particularly, $L^1$ and $L^2$ are each independently a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. More particular still, $L^1$ and $L^2$ are each independently -alkyl- or -substituted alkyl-. More particular still, $L^1$ and $L^2$ are independently —$C_{3-8}$ alkyl- or substituted alkyl.

In another embodiment, the compound has the structure:

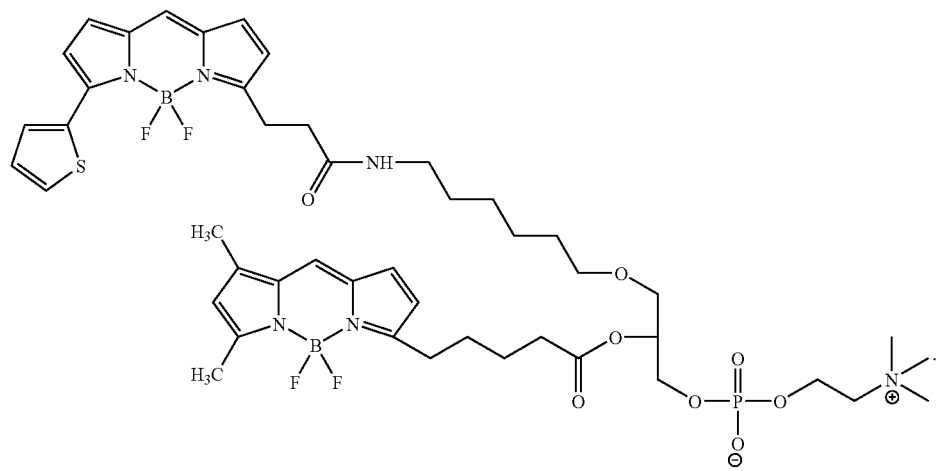

Synthesis

Typically the synthetic methodology used to prepare the compounds of the invention involves preparation of the phospholipase $A_2$ substrate first followed by conjugation to the FRET pair comprising an acceptor and donor molecule. This can be achieved by a variety of synthetic operations. Preparation of the substrate is done in such a way so as to include a nucleophilic or electrophilic moiety which can affect conjugation of the linker either directly or through a linker moiety. Alternatively a nucleophilic or electrophilic moiety on the linker is covalently attached to the acceptor or donor molecule either before or after attachment to the substrate. The order of attachment can be reversed.

One preferred method of synthesis is provided in Scheme 2:

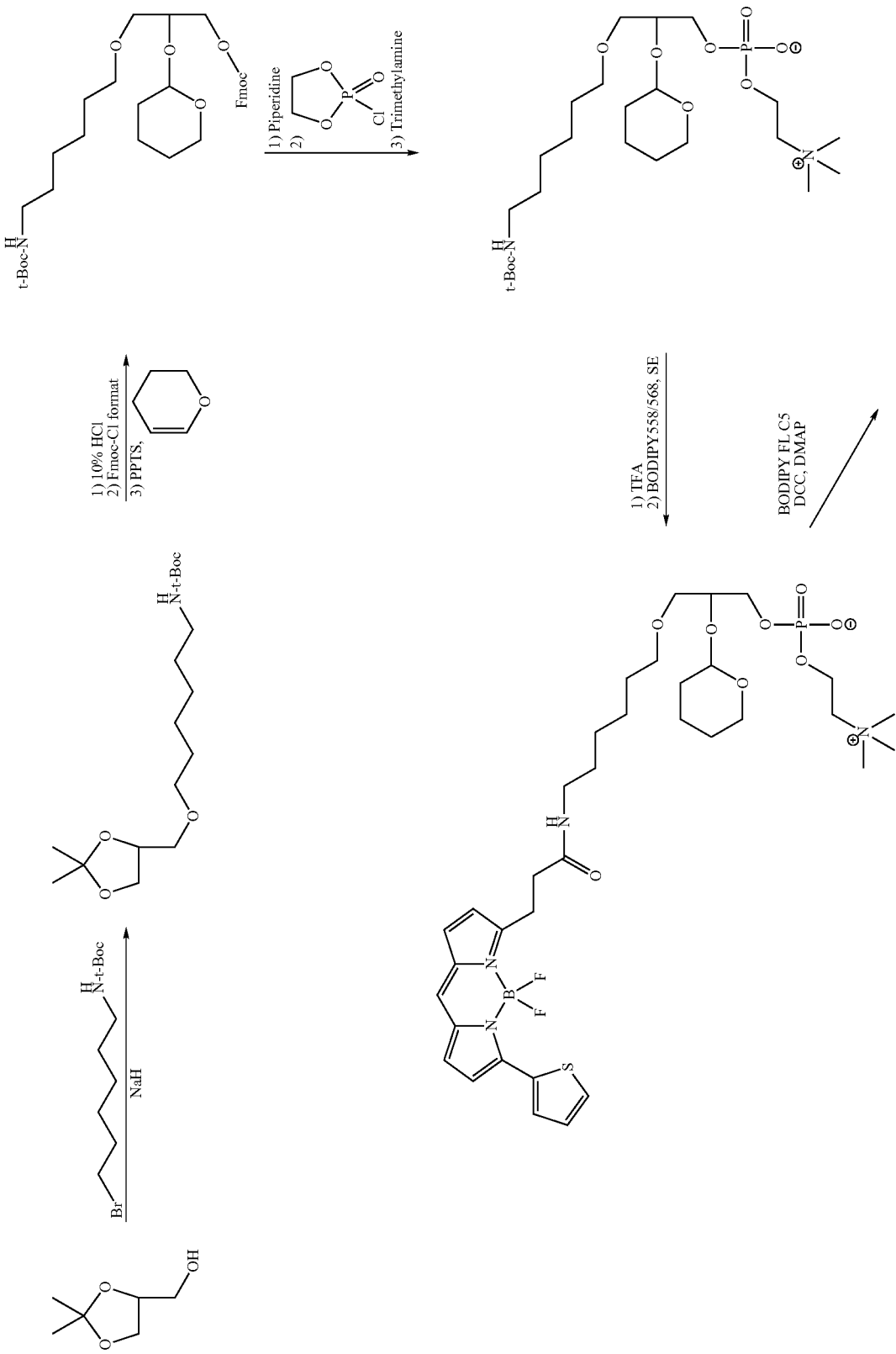

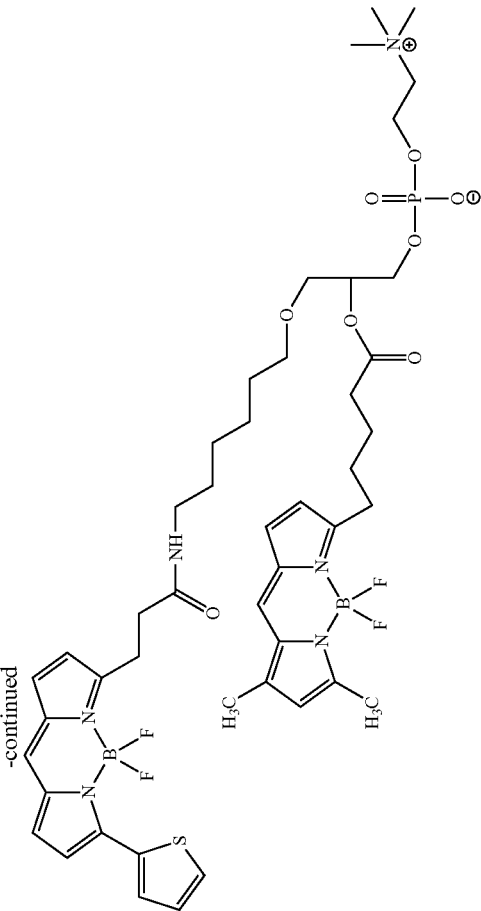

Method of Use

The compounds of the invention are useful for any application where it is desirable to detect or quantitate the activity of $PLA_2$. In order for a particular compound of the present invention to be useful for detection purposes, it must exhibit a detectable change in spectral properties from a first signal to a second signal upon contact/cleavage by $PLA_2$. Preferably the change in spectral properties is a ratiometric change in fluorescence properties, which is observed as a wavelength change of cleaved verses un-cleaved $PLA_2$ substrate. In one embodiment, the instant compounds display a shift in emission wavelength from Red to green upon cleavage of the donor molecule or acceptor from the $PLA_2$ substrate.

A preferred aspect of the present invention involves a method for detecting phospholipase $A_2$ ($PLA_2$) activity in a sample, comprising:

contacting the sample with a compound of formula:

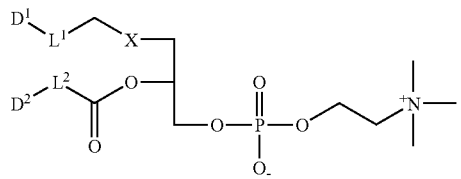

wherein,
$D^1$ is a borapolyazaindacene fluorophore;
$D^2$ is a borapolyazaindacene fluorophore;
$L^1$ is a linker;
$L^2$ is a linker; and
X is —O—, —S— or —NH—;
or a salt, stereoisomer, or tautomer thereof;
wherein $D^1$ and $D^2$ exhibit fluorescence resonance energy transfer (FRET) and generate a first signal;
incubating the sample and compound for sufficient time for -$L^2$-$D^2$ to be cleaved if $PLA_2$ is in the sample; and
illuminating the sample with an appropriate wavelength, wherein $PLA_2$ activity is detected by a change in fluorescence to a second signal.

In a more particular embodiment, the sample comprises cells. In another embodiment, the incubating step comprises incubating the sample and compound for sufficient time to allow the compound to enter a cell.

A specific indicator of the present invention is useful for the detection and/or quantification of $PLA_2$ activity, when cleavage of the acceptor/donor moiety by $PLA_2$ results in a detectable change in spectral properties. Preferably, the change in spectral properties is a detectable fluorescence response.

The optical response of the indicating reagent is determined by a change in absorbance or fluorescence, preferably fluorescence. For fluorescence measurements, the concentration or activity level of $PLA_2$ will depend mostly on the sensitivity of the equipment used for its detection.

For $PLA_2$ detection, the substrate is combined with a sample in a way that will facilitate detection of the enzyme concentration in the sample. The sample is generally a representative cell population, fluid or liquid suspension that is known or suspected to contain $PLA_2$. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors.

In one embodiment of the invention, the sample contains cells, and the indicator is combined with the sample in such a way that the indicator is present within the sample cells. By selection of appropriate substituents, indicators are prepared that will selectively localize in desired locations of the cells, and provide measurements of $PLA_2$ activity in those locations. Lipophilic substituents will result in localization in lipophilic environments in the cell, such as cell membranes. Selection of cationic indicators will typically result in localization of the indicator in mitochondria.

In one embodiment, the compounds of the invention, in any of the embodiments described above, are associated, either covalently or non-covalently, with a surface such as a microfluidic chip, a silicon chip, a microscope slide, a microplate well, or another solid matrix, and is combined with the sample of interest as it flows over the surface. The detectable optical response is therefore detected on the matrix surface itself, typically by use of an instrumental. This embodiment of the invention is particularly suited to high-throughput screening using automated methods.

Quantification of $PLA_2$ levels in samples is typically accomplished using the indicators of the present invention by methods known in the art. In a preferred embodiment, the ratiometric measurement of $PLA_2$ concentration provides accurate measurement of enzyme concentrations by the treatment of the fluorescence data as the ratio of excitation or fluorescence intensities at two wavelengths, rather than the absolute intensity at a single wavelength. Where cleavage of the FRET pair produces a distinct signal, the shift in fluorescent intensity away from that of the FRET pair, indicates presence of the $PLA_2$ enzyme.

The optical response of the indicator to the enzyme can be detected by various means that include measuring fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator is covalently attached to the fiber optic probe material, typically glass or functionalized glass (e.g., aminopropyl glass) or the indicator is attached to the fiber optic probe via an intermediate polymer, such as polyacrylamide. The indicator solution is alternatively incorporated non-covalently within a fiber optic probe, as long as there is a means whereby the $PLA_2$ enzyme can come into contact with the indicator solution.

Kits of the Invention

Due to the advantageous properties and the simplicity of use of the instant $PLA_2$ indicator compounds, they are particularly useful in the formulation of a kit for the detection, quantification or monitoring of $PLA_2$ activity, comprising one or more compounds or compositions of the invention in any of the embodiments described above (optionally in a stock solution), instructions for the use of the compound to complex or detect $PLA_2$ activity, and optionally comprising additional components. In one aspect, the compounds of the invention are associated with a surface, such as a chip, microplate well, or other solid matrix, and the sample of interest flows over the surface. The detectable optical response is therefore detected on the matrix surface itself.

A particular kit for detecting phospholipase $A_2$ ($PLA_2$) activity, comprising:
a compound of formula:

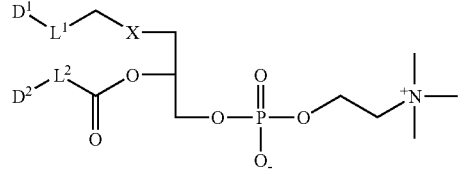

wherein,

D¹ is a borapolyazaindacene fluorophore;

D² is a borapolyazaindacene fluorophore;

L¹ is a linker;

L² is a linker; and

X is —O—, —S— or —NH—;

or a salt, stereoisomer, or tautomer thereof;

wherein D¹ and D² exhibit fluorescence resonance energy transfer (FRET); and one or more components selected from the group consisting of written instructions, a standard, a control, a vial, an aqueous buffer solution and an organic solvent.

Additional kit components are present as pure compositions, or as aqueous solutions that incorporate one or more additional kit components. Any or all of the kit components optionally further comprise buffers.

Illumination:

In a typical detection method, at any time after or during contact of the compounds of the present invention with a sample suspected of containing $PLA_2$, the sample is visualized whereby the compound is detected. Visualization can comprise different methods and is dependent on the FRET pair that is covalently attached to the $PLA_2$ substrate. Typically visualization comprises illumination with a wavelength of light capable of exciting the one of the dyes to produce a detectable optical response, as defined above, and observed with a means for detecting the optical response. More particularly, the compound may be illuminated at least twice, before contact with the sample suspected of containing $PLA_2$ and during or after contact. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence-based microplate readers, standard or minifluorometers, or chromatographic detectors. The degree and/or location of enzyme activity, compared with a standard or expected response and/or pre-contact response, indicates whether and to what degree the sample possesses a given characteristic, i.e., cell processes/activity.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, fluorescence-based microplate readers, or by a means for amplifying the signal such as photomultiplier tubes.

Thus, it is contemplated by the present invention that a wide variety of instrumentation may be used to detect $PLA_2$ activity.

As described above, while a wide variety of methods of detection are used with the present invention, a preferred method includes the use of fluorescence resonance energy transfer (FRET). Fluorescence from the FRET pair and/or cleaved donor and acceptor molecule can be visualized with a variety of imaging techniques, including ordinary light or fluorescence microscopy. Filters may be used to separate and or detect particular wavelengths of the dyes and ratiometric increase of one particular dye or a change in wavelength of the signal generated.

The examples below are given so as to illustrate the practice of this invention. They are not intended to limit or define the entire scope of this invention.

EXAMPLES

Example 1

1-O-(6-(t-BOC-amino)hexyl)-2,3-O-(isopropylidene)-sn-glycerol

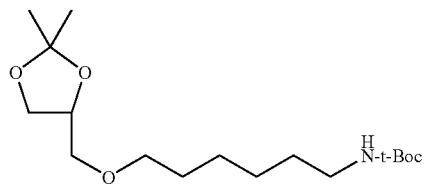

Compound 1

To a solution of (R)-(−)-2,2-dimethyl-1,3-dioxolane-4-methanol (1.17 g, 8.85 mmol) in 30 ml of dry DMF was added sodium hydride (390 mg, 9.7 mmol) and the mixture was stirred at room temperature under $N_2$ atmosphere for 1 hour. To the mixture was added a solution of 6-(t-BOC-amino) hexyl bromide (2.5 g, 8.85 mmol) in 25 ml of dry DMF over 30 minutes. After stirring at room temperature overnight, DMF was removed in vacuo and the resulting residue was treated with 5% methanol in chloroform (100 ml). It was filtered, concentrated in vacuo and the resulting crude product was purified by column chromatography on silica gel eluting with 5% methanol in chloroform to give 2 g of product.

Example 2

1-O-(6-(t-BOC-amino)hexyl)-sn-gycerol

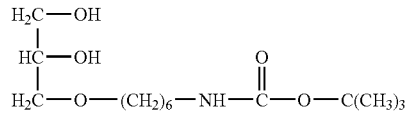

Compound 2

To a solution of 1-O-(6-(t-BOC-amino)hexyl)-2,3-O-(isopropylidene)-sn-glycerol (2.0 g, 6.03 mmol) in 10 ml of methanol was added 5 ml of 10% HCl. After stirring at room temperature for 30 minutes, the reaction mixture was diluted with chloroform, washed with dilute $NaHCO_3$ and water. The separated organic layer was dried over $Na_2SO_4$ and concentrated in vacuo to give 1.2 g of product as colorless oil.

Example 3

1-O-(6-(t-BOC-amino)hexyl)-3-O-(FMOC)-sn-glycerol

Compound 3

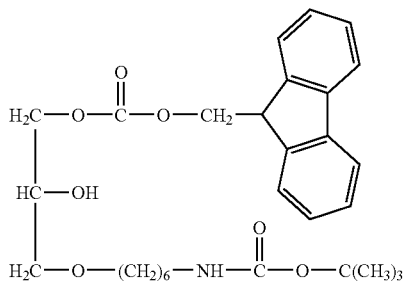

To a solution of 1-O-(6-(t-BOC-amino)hexyl)-sn-gycerol (1.2 g, 4.1 mmol) and 4-dimethylaminopyridine (250 mg, 2.1 mmol) in 100 ml of dry dichloromethane was added a solution of FMOC chloride (530 mg, 2.1 mmol) in 30 ml of dry dichloromethane slowly over 30 minutes at −10° C. After removing the solvent in vacuo, the resulting crude product was purified by column chromatography over silica gel eluting with 1:1/ethyl acetate:hexanes to give 855 mg of product.

Example 4

1-O-(6-(t-BOC-amino)hexyl)-2-O-(tetrahydropyranyl)-3-O-(FMOC)-sn-gylcerol

Compound 4

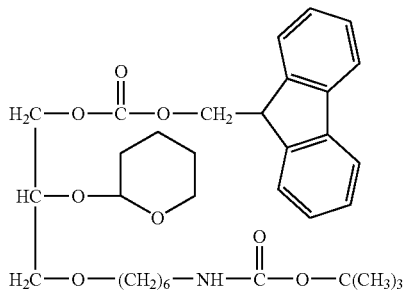

To a solution of 1-O-(6-(t-BOC-amino)hexyl)-3-O-(FMOC)-sn-glycerol (725 mg, 1.4 mmol) in 25 ml of dry dichloromethane was added 3,4-dihydro-2H-pyran (0.3 ml, 3.2 mmol) followed by addition of pyridinium p-toluenesulfonate. After stirring at room temperature under $N_2$ atmosphere for 2 hours, the reaction mixture was diluted with chloroform (100 ml), washed with water (2×40 ml), dried over $Na_2SO_4$ and concentrated in vacuo to give 840 mg of product as colorless oil.

Example 5

1-O-(6-(t-BOC-amino)hexyl)-2-O-(terahydropyranyl)-sn-glycerol

Compound 5

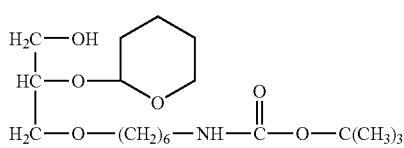

To a solution of 1-O-(6-(t-BOC-amino)hexyl)-2-O-(tetrahydropyranyl)-3-O-(FMOC)-sn-gylcerol (840 mg, 1.40 mmol) in 1 ml of dichloromethane was added a solution of piperidine (415 ul, 4.2 mmol) in 1 ml of dichloromethane and the mixture was stirred at room temperature for 2 hours. The reaction mixture was diluted with chloroform (150 ml), washed with 0.5% HCl (3×50 ml), dried over $Na_2SO_4$ and concentrated in vacuo to give a crude product. It was purified by column chromatography over silica gel eluting with 1:1 (ethyl acetate:haxanes) to give 220 mg of product.

Example 6

1-O-(6-(t-BOC-amino)hexyl)-2-O-(tetrahydropyranyl)-sn-glycerol-3-phosphocholine

Compound 6

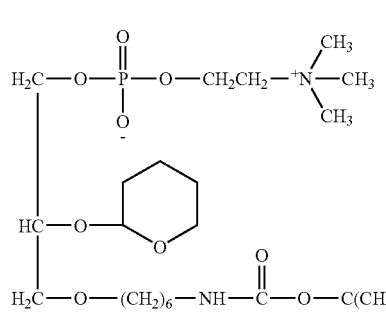

To a solution of 1-O-(6-(t-BOC-amino)hexyl)-2-O-(terahydropyranyl)-sn-glycerol (100 mg, 0.27 mmol) in 1 ml of toluene were added N,N-diisopropylethylamine (56 ul, 0.32 mmol) and 2-chloro-1,3,2-dioxaphospholane-2-oxide (56 ul, 0.32 mmol). After stirring at room temperature under $N_2$ atmosphere overnight, toluene was removed in vacuo. The resulting residue was dissolved in acetonitrile (3 ml) and transferred into a pressure bottle. Trimethylamine (~2 ml) was added after the pressure bottle was cooled with dry ice. The pressure bottle was sealed and stirred at 65° C. for 24 hours. After cooling down to room temperature, solvent was removed in vacuo and the resulting crude product was purified by column chromatography over silica gel (eluting first with 10% methanol in chloroform and finally with 4:30:66 (water:methanol:chloroform)) to give 60 mg of product.

Example 7

1-O-(6-aminohexyl)-sn-glycerol-3-phosphocholine, trifluoroacetic acid salt

Compound 7

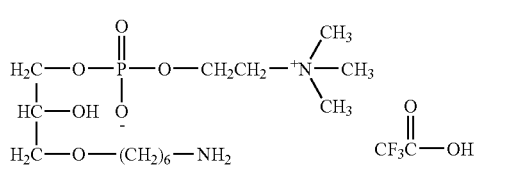

To a sample of 1-O-(6-(t-BOC-amino)hexyl)-2-O-(tetrahydropyranyl)-sn-glycerol-3-phosphocholine (30 mg, 0.056 mmol) was added trifluoroacetic acid (~50 ul) and the mixture was stirred at room temperature for 15 minutes. Solvent was removed in vacuo and the resulting residue was washed with ether and dried to give 25 mg of product.

Example 8

1-O-(6-BODIPY 558/568-aminohexyl)-sn-glycerol-3-phosphocholine

Compound 8

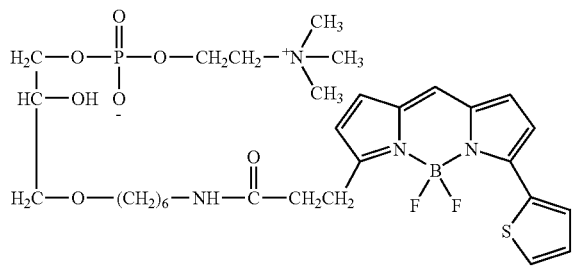

To a solution of 1-O-(6-aminohexyl)-sn-glycerol-3-phosphocholine, trifluoroacetic acid salt (30 mg, 0.06 mmol) in 1 ml of DMF were added triethylamine (100 ul, 0.70 mmol) and BODIPY 558/568, SE (56 mg, 0.13 mmol) and the mixture was stirred at room temperature for 10 minutes. After removing DMF in vacuo, the resulting residue was purified by column chromatography over silica gel eluting with 20% water in acetonitrile to give 40 mg of product.

Example 9

1-O-(6-BODIPY 558/568-aminohexyl)-2-BODIPY FL $C_5$-sn-glycerol-3-phosphocholine Compound 9

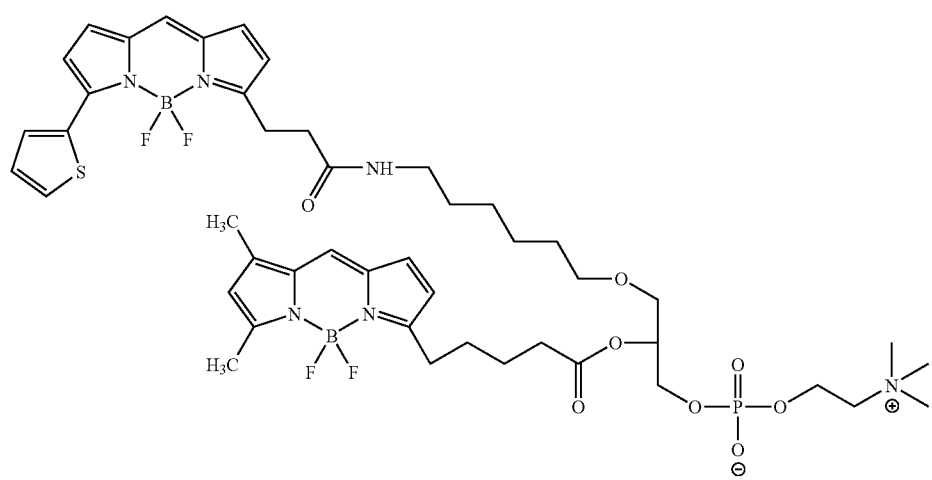

To a suspension of 1-O-(6-BODIPY 558/568-aminohexyl)-sn-glycerol-3-phosphocholine (7 mg, 0.01 mmol), BODIPY FL $C_5$ (8 mg, 0.02 mmol), 4-dimethylaminopyridine (1.5 mg, 0.01 mmol) in 6 ml of dichloromethane was added 1,3-dicyclohexyl carbodiimide and the mixture was stirred for 2 days. The reaction mixture was diluted with dichloromethane, washed with saturated citric acid (2×20 ml), dried over $Na_2SO_4$ and concentrated. The resulting crude product was purified by column chromatography over silica gel (first eluting with 5% water in acetonitrile and finally with 15% water in acetonitrile) to give 8 mg of desired product as an orange-red solid.

Example 10

$PLA_2$ Activity on the Substrate

A lipid mixture was prepared by mixing 30 uL of 10 mM dioleoylphosphatidylcholine (DOPC) in ethanol, 30 uL of 10 mM dioleoylphophatidylgylcerol (DOPG) in ethanol and 6 uL of 1 mM the Example 9 in ethanol. The liposome preparation was done by adding 50 uL of the above lipid mixture slowly over a period of one minute into 5 ml of assay buffer solution (50 mM TRIS, 100 mM NaCl, 1 mM $CaCl_2$). The resulting substrate liposome mixture (500 uL) and assay buffer solution were mixed in a cuvette (Starna 9F-Q-10) and fluorescence was measured by exciting at 460 nm as a control (t=0 min). To monitor the enzyme activity, 500 uL of the resulting substrate liposome mixture and 500 uL of 5 U/mL of Bee Venom $PLA_2$ enzyme were mixed in a cuvette (resulting enzyme concentration, 2.5 U/mL) and fluorescence was measured at 1 minute (t=1 min) and every 5 minutes for an hour. Fluorescence was measured with Perkin Elmer LS50B Luminescence Spectrometer by exciting at 460 nm at ambient temperature. The fluorescence intensity ratio change, 512/574 nm, was plotted over time. Results are shown in FIG. 1.

Example 11

Kinetic Study with $PLA_2$

Figure 2A:
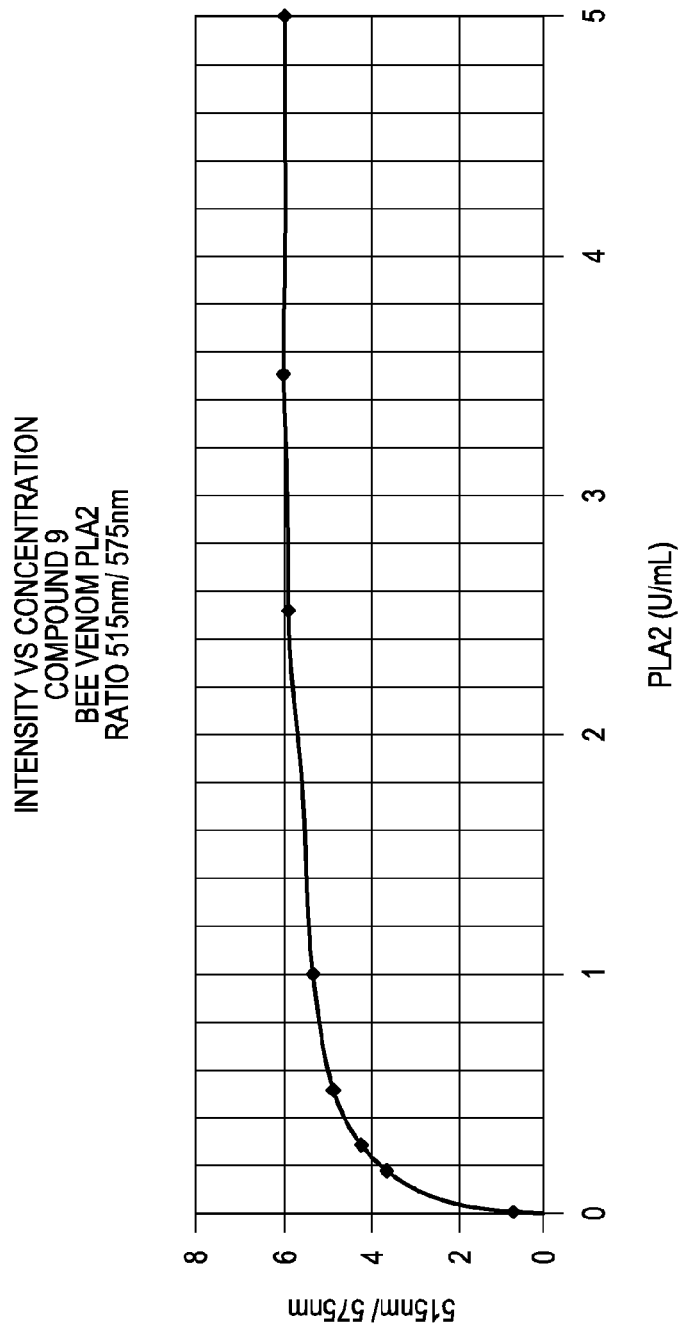
FIG. 2A depicts the kinetics of Example 9 by showing the fluorescence ratio change, 515/575 nm over enzyme concentration at 21 minutes.
Figure 2B:
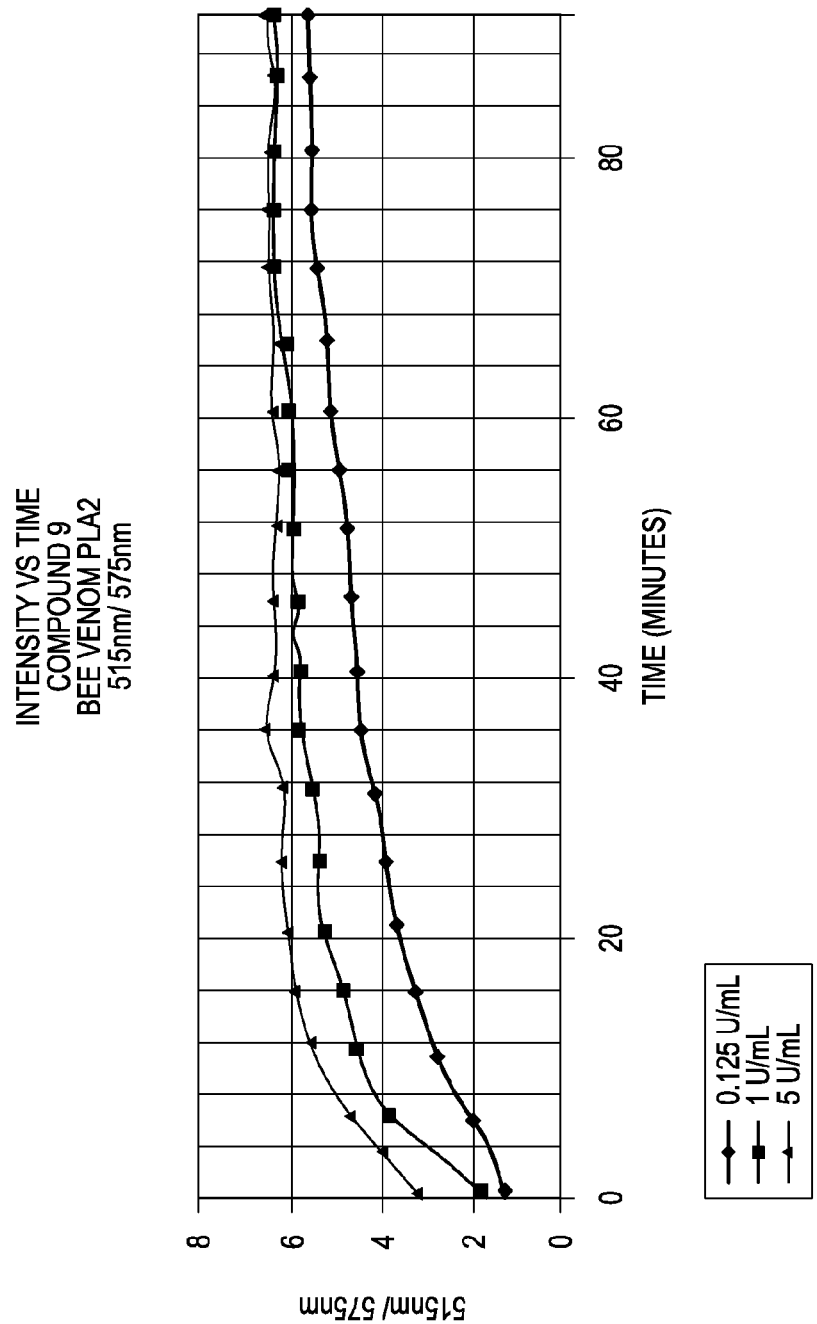
FIG. 2B demonstrates the enzyme kinetic activity by showing fluorescence ratio change 515/575 nm over time at three different enzyme concentrations.

A lipid mixture was prepared by mixing 30 uL of 10 mM dioleoylphosphatidylcholine (DOPC) in ethanol, 30 uL of 10 mM dioleoylphophatidylgylcerol (DOPG) in ethanol and 30 uL of 1 mM the substrate (D287-022-AC) in ethanol. The liposome preparation was done by adding 50 uL of the above lipid mixture slowly over a period of one minute into 5 ml of assay buffer solution (50 mM TRIS, 100 mM NaCl, 1 mM $CaCl_2$. Using a Corning 96-Well, Flat Bottom Well Plate, loaded wells A through H, #'s 4-6 (24 wells loaded-to yield triplicates of each enzyme concentration) with 50 uL of the substrate-liposome mixture above. The Microplate Reader was set up with Molecular Devices Spectra Max M5 at 37° C. exciting at 460 nm and reading wells at 515 nm and at 575 nm. Quickly add 50 uL per well of $PLA_2$ enzyme (Bee Venom)/ control to wells. Immediately commenced fluorescence measurements (t=1 min), and then every 5 minutes for an hour. Results are shown in FIG. 2.

Example 12

Figure 3:
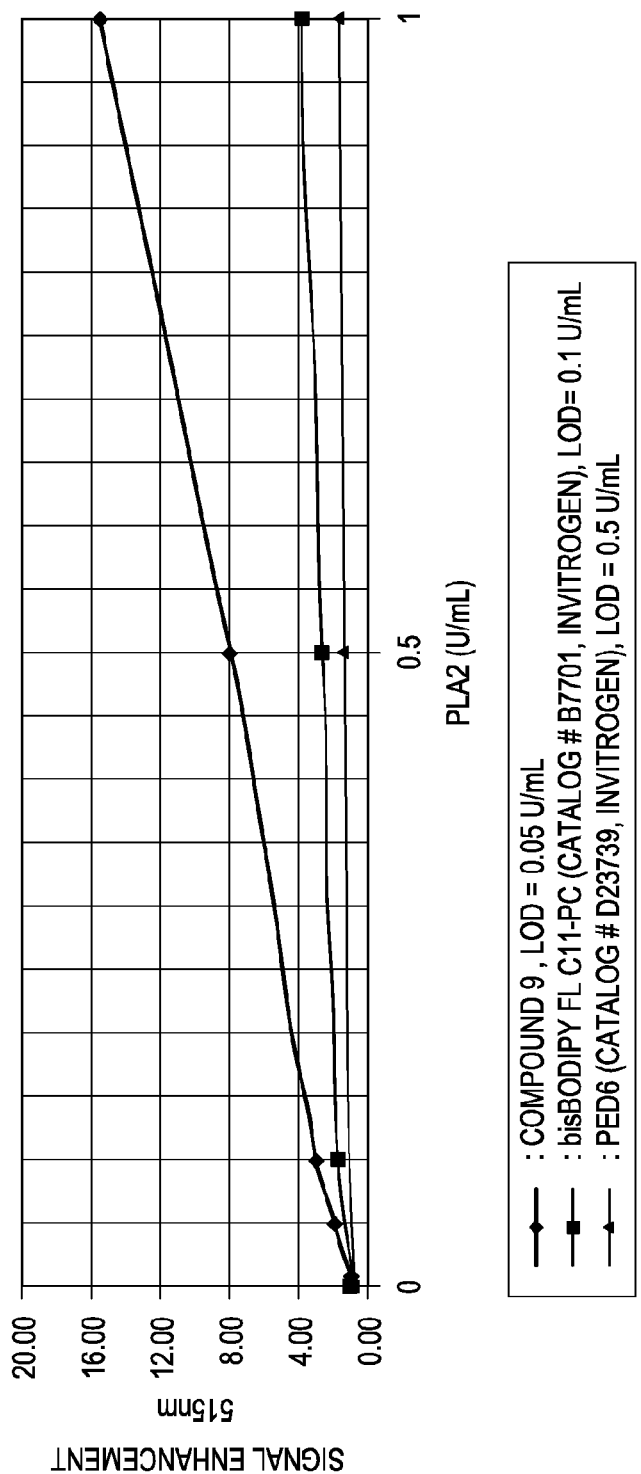
FIG. 3 depicts the limit of labeling (LOD) comparison of Compound 9 substrate with commercially available substrates (bisBODIPY FL C11-PC and PED6) with bee venom PLA$_2$, plotted signal enhancement ratio (I/I$_0$) at different enzyme concentrations between 0.001 U/mL and 1 U/mL).

Limit of Detection (LOD) Comparison of the Substrate Compound 9 with Commercially Available Substrates with Bee Venom PLA$_2$ The enzyme reaction of bee venom PLA$_2$ with substrates Compound 9, bisBODIPY FL C11-PC (available from Invitrogen, catalog #B7701) and PED6 (available from Invitrogen, catalog #D23739) was done by following the protocol as described in Example 11 with lower concentration ranges of enzyme (0.001 U/mL~1 U/mL) for each substrate (1.65 uM). The relative fluorescence intensity at 515 nm (exciting at 460 nm) for each was measured before ($I_0$) and after (I) addition of enzyme (10 minutes). The ratio of signal enhancement ($I/I_0$) change for each substrate was plotted over different concentrations of bee venom PLA$_2$ (0.001, 0.005, 0.01, 0.05, 0.1, 0.5 and 1 U/mL). Results are shown in FIG. 3.

32. The compound of claim 1, wherein the compound has the formula:
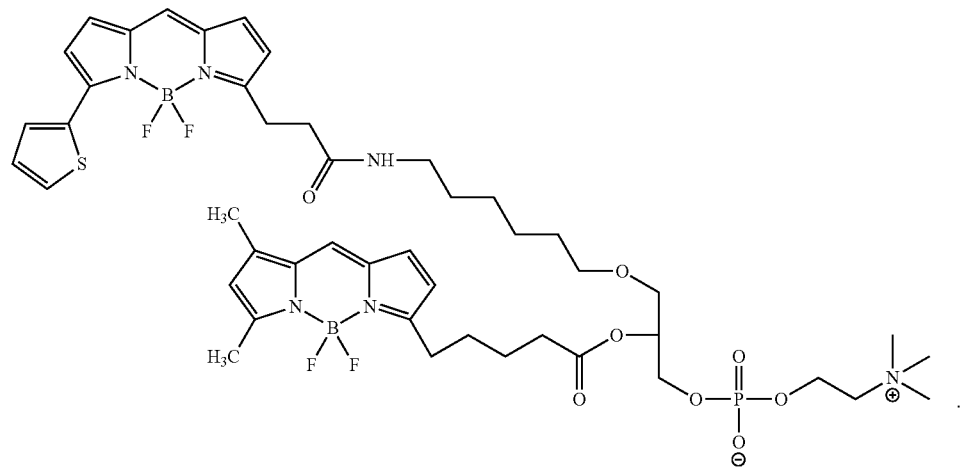

The invention claimed is:

1. A compound of the formula:

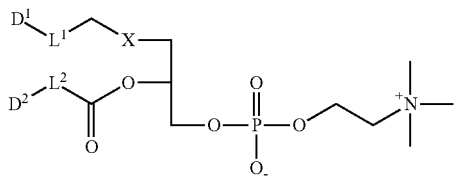

wherein,
D$^1$ is a 4,4-difluoro-4-bora-3a,4a-diaza-s-indacene (BODIPY);
D$^2$ is a 4,4-difluoro-4-bora-3a,4a-diaza-s-indacene (BODIPY);
L$^1$ is a linker;
L$^2$ is a linker; and
X is —O—, —S— or —NH—;
or a salt, stereoisomer, or tautomer thereof;
wherein D$^1$ and D$^2$ exhibit fluorescence resonance energy transfer (FRET).

2. The compound of claim 1, wherein D$^1$ is a donor and D$^2$ is an acceptor.

3. The compound of claim 1, wherein D$^2$ is substituted with an aryl or heteroaryl group.

4. The compound of claim 1, wherein D$^1$ is:

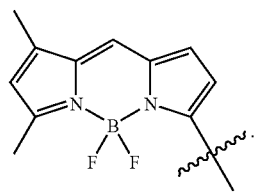

5. The compound of claim 3, wherein D$^2$ is:

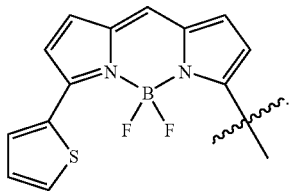

6. The compound of claim 1, wherein X is —O—.
7. The compound of claim 1, wherein L$^1$ is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.
8. The compound of claim 1, wherein L$^1$ is -alkyl- or -substituted alkyl-.
9. The compound of claim 1, wherein L$^2$ is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.
10. The compound of claim 1, wherein L$^2$ is -alkyl- or -substituted alkyl-.
11. The compound of claim 1, wherein L$^1$ and L$^2$ are independently —C$_{3-8}$ alkyl-.
12. A compound of formula:

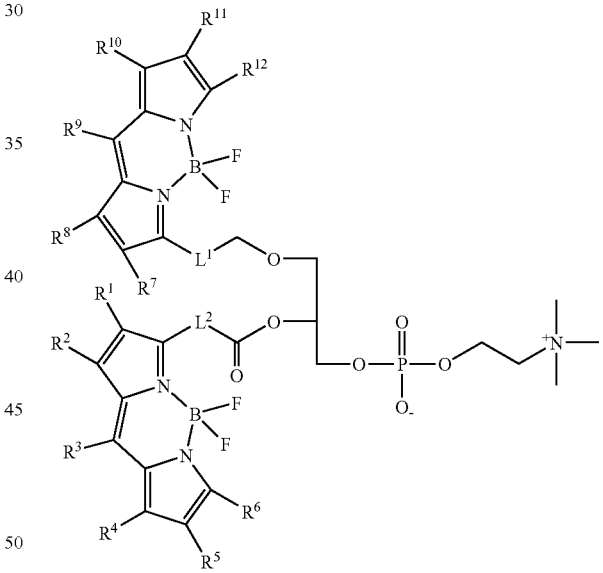

wherein,
L$^1$ is a linker;
L$^2$ is a linker;
R$^1$, R$^2$, R$^3$, R$^4$, R$^5$ and R$^6$ are each independently selected from the group consisting of H, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^7$, $R^8$, $R^9$, $R^{10}$, $R^{11}$ and $R^{12}$ are each independently selected from the group consisting of H, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

13. The compound of claim 12, wherein $R^1$, $R^2$, $R^3$, $R^4$, $R^5$ and $R^6$ are each independently selected from the group consisting of H, halo, alkyl or substituted alkyl.

14. The compound of claim 12, wherein $R^7$, $R^8$, $R^9$, $R^{10}$, $R^{11}$ and $R^{12}$ are each independently selected from the group consisting of H, aryl, substituted aryl, heteroaryl, substituted heteroaryl.

15. The compound of claim 14, wherein at least one of $R^7$, $R^8$, $R^9$, $R^{10}$, $R^{11}$ and $R^{12}$ is aryl, substituted aryl, heteroaryl, substituted heteroaryl.

16. The method of claim 12, wherein $R^6$ is heteroaryl.

17. The method of claim 12, wherein $R^6$ is thiophenyl.

18. The method of claim 12, wherein $R^1$, $R^2$, $R^3$, $R^4$ and $R^5$ are H.

19. The method of claim 12, wherein $R^{10}$ and $R^{12}$ are methyl.

20. The method of claim 12, wherein $R^7$, $R^8$, $R^9$, and $R^{11}$ are H.

21. The compound of claim 12, wherein $L^1$ and $L^2$ are each independently a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

22. The compound of claim 12, wherein $L^1$ and $L^2$ are each independently -alkyl- or -substituted alkyl-.

23. The compound of claim 12, wherein $L^1$ and $L^2$ are independently $-C_{3-8}$ alkyl-.

24. A compound of formula:

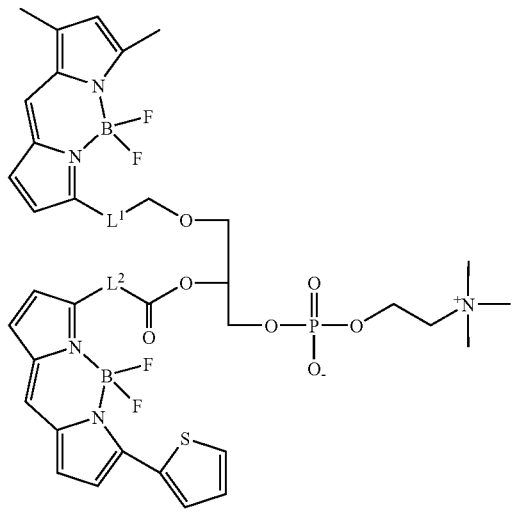

wherein,
$L^1$ is a linker; and
$L^2$ is a linker.

25. The compound of claim 24, wherein $L^1$ and $L^2$ are each independently a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

26. The compound of claim 24, wherein $L^1$ and $L^2$ are each independently -alkyl- or -substituted alkyl-.

27. The compound of claim 24, wherein $L^1$ and $L^2$ are independently $-C_{3-8}$ alkyl-.

28. A method for detecting phospholipase $A_2$ ($PLA_2$) activity in a sample, comprising:
contacting the sample with a compound of formula:

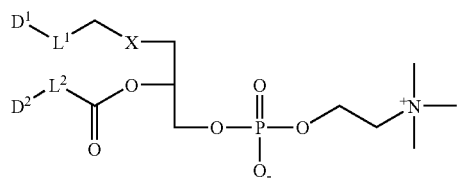

wherein,
$D^1$ is a 4,4-difluoro-4-bora-3a,4a-diaza-s-indacene (BODIPY);
$D^2$ is a 4,4-difluoro-4-bora-3a,4a-diaza-s-indacene (BODIPY);
$L^1$ is a linker;
$L^2$ is a linker; and
X is —O—, —S— or —NH—;
or a salt, stereoisomer, or tautomer thereof;
wherein $D^1$ and $D^2$ exhibit fluorescence resonance energy transfer (FRET) generating a first fluorescent signal;
incubating the sample and compound for sufficient time for $-L^2-D^2$ to be cleaved if $PLA_2$ is in the sample; and
illuminating the sample with an appropriate wavelength, wherein $PLA_2$ activity is detected by a change in fluorescence to a second fluorescent signal.

29. The method of claim 28, wherein the sample comprises cells.

30. The method of claim 28, wherein the incubating step comprises incubating the sample and compound for sufficient time to allow the compound to enter a cell.

31. A kit for detecting phospholipase $A_2$ ($PLA_2$) activity, comprising: a compound of formula:

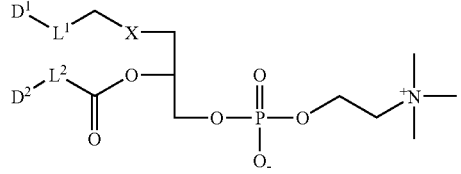

wherein,
$D^1$ is a 4,4-difluoro-4-bora-3a,4a-diaza-s-indacene (BODIPY);
$D^2$ is a 4,4-difluoro-4-bora-3a,4a-diaza-s-indacene (BODIPY);
$L^1$ is a linker;
$L^2$ is a linker; and
X is —O—, —S— or —NH—;
or a salt, stereoisomer, or tautomer thereof;
wherein $D^1$ and $D^2$ exhibit fluorescence resonance energy transfer (FRET); and
one or more components selected from the group consisting of written instructions, a standard, a control, a vial, an aqueous buffer solution and an organic solvent.